United States Patent [19]

Alpern

[11] Patent Number: 4,511,035
[45] Date of Patent: Apr. 16, 1985

[54] PACKAGE FOR SURGICAL INSTRUMENT

[75] Inventor: Marvin Alpern, Glen Ridge, N.J.

[73] Assignee: Ethicon, Inc., Somerville, N.J.

[21] Appl. No.: 457,821

[22] Filed: Jan. 13, 1983

[51] Int. Cl.³ .............................................. B65D 83/10
[52] U.S. Cl. .................................... 206/363; 206/339
[58] Field of Search ............... 206/363, 339, 349, 368, 206/369, 370, 372, 373, 374, 375

[56] References Cited

U.S. PATENT DOCUMENTS

| | | | |
|---|---|---|---|
| 1,644,830 | 10/1927 | Henderson | 206/363 |
| 2,804,969 | 9/1957 | Barnett | 206/363 |
| 3,126,629 | 3/1964 | Claisse et al. | 206/363 |
| 3,704,096 | 11/1972 | Verses et al. | 206/363 |
| 4,229,420 | 10/1980 | Smith et al. | 206/363 |
| 4,385,692 | 5/1983 | Eldridhg, Jr. | 206/363 |
| 4,402,407 | 9/1983 | Maly | 206/363 |
| 4,408,603 | 10/1983 | Blake et al. | 206/339 |
| 4,412,617 | 11/1983 | Cerwin | 206/339 |

*Primary Examiner*—Joseph Man-Fu Moy
*Attorney, Agent, or Firm*—Robert L. Minier

[57] ABSTRACT

An improved package for sterile surgical instruments. The package includes means for holding the instrument. The package also includes means for maintaining the instrument in a position so that moveable parts do not take a permanent set. The package is constructed to provide for ready access to the instrument while maintaining the instrument in a sterile condition.

10 Claims, 6 Drawing Figures

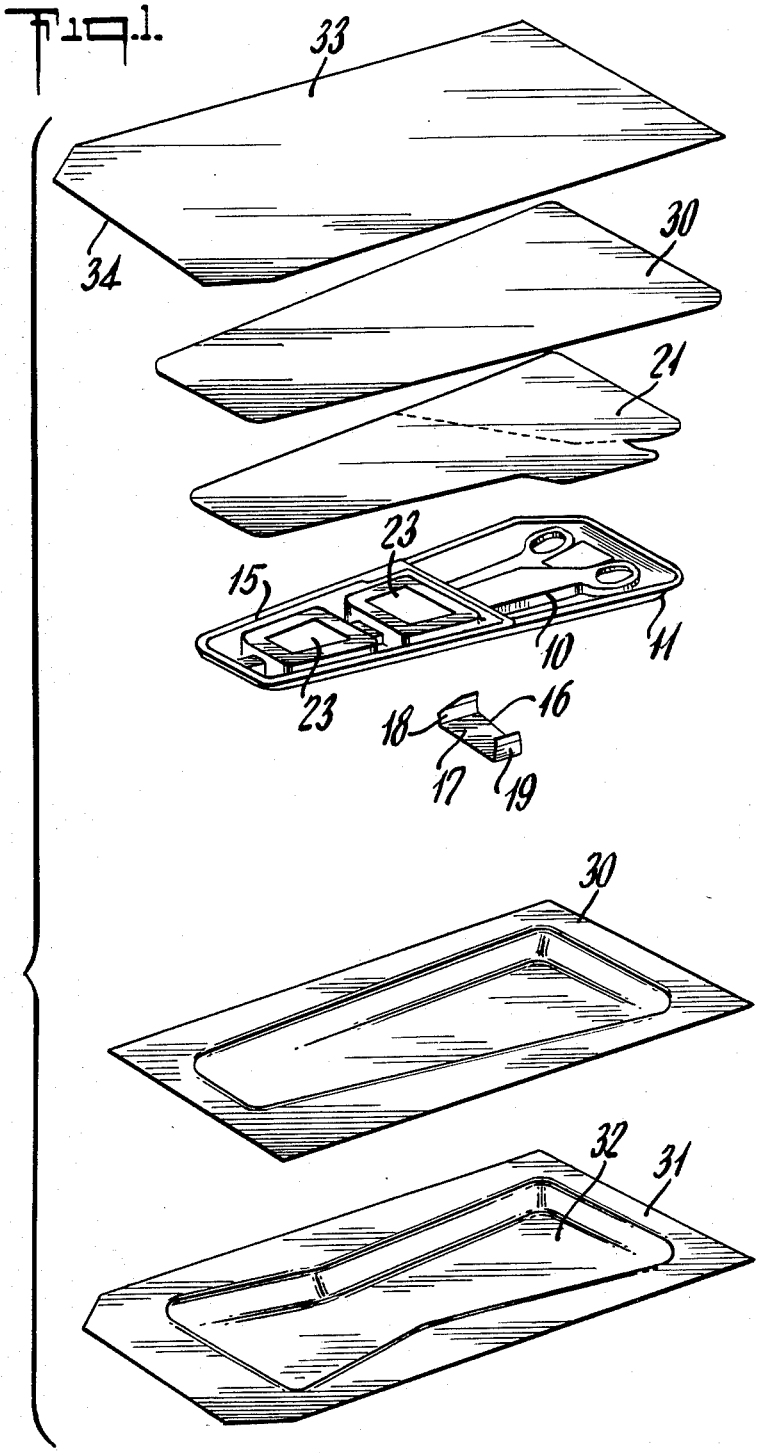

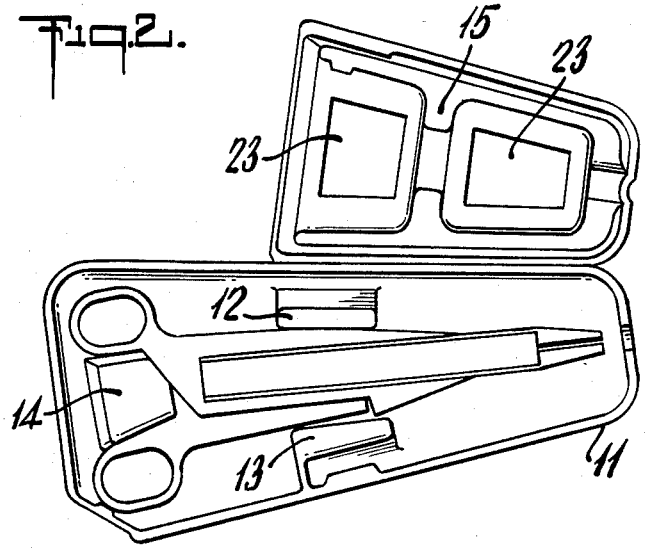
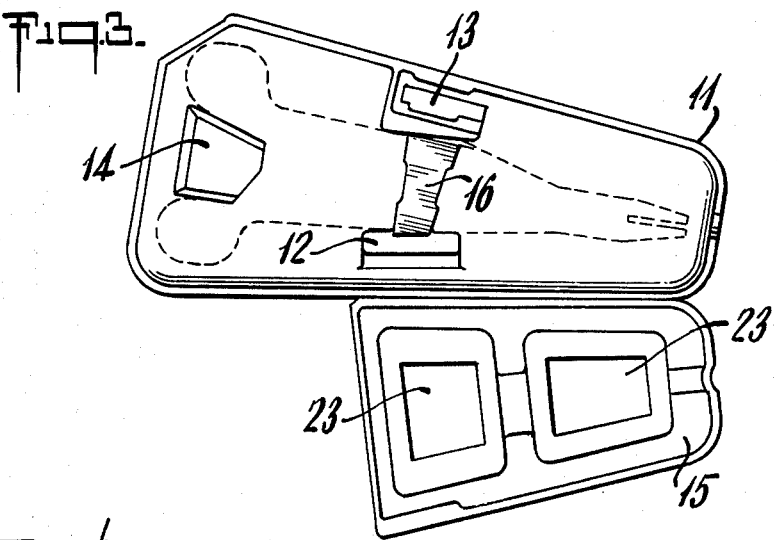
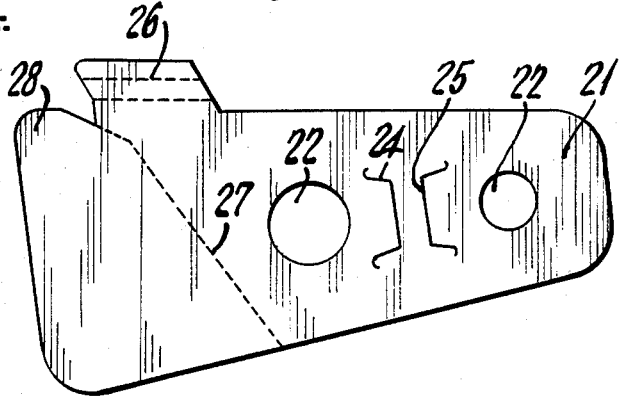

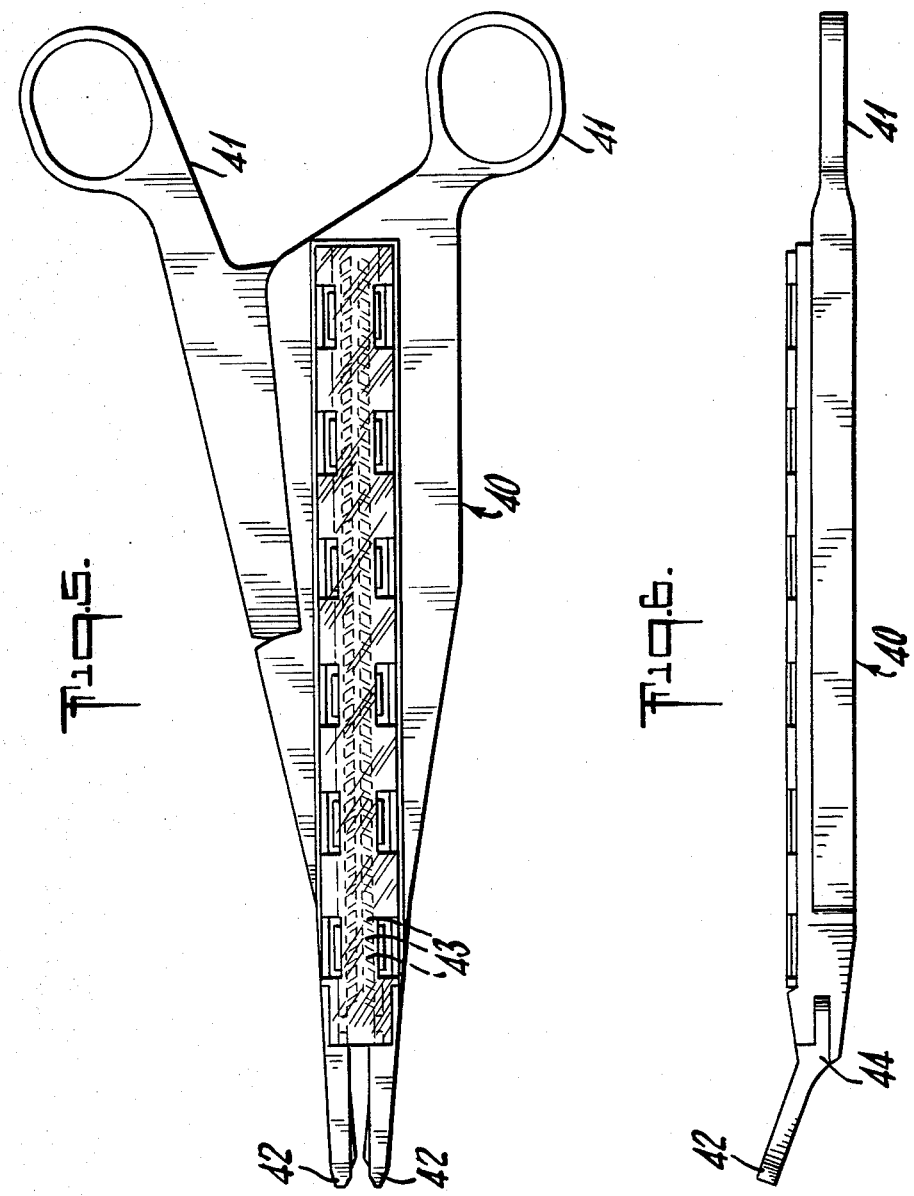

4,511,035

PACKAGE FOR SURGICAL INSTRUMENT

BACKGROUND OF THE INVENTION

Surgical instruments are widely known and have been used for some time now in various surgical procedures. In recent years, surgical instruments for applying staples or other fasteners for closing wounds, as well as instruments for occluding or ligating various tubular vessels, such as blood vessels, have been developed. These instruments for closing wounds apply a plurality of staples or other types of fasteners and apply the fasteners either in a repeating mode; that is, one fastener after another each time the instrument is actuated, or as a series of fasteners at a single time on one actuation of the instrument. These types of repeating surgical instruments may be classified as automatic or semi-automatic and greatly reduce the time involved in certain aspects of a surgical procedure. The instruments continue to gain acceptance in the surgical community. One problem with these instruments is that after they have been used they need to be thoroughly cleaned and sterilized and reloaded with new fasteners to be used repeated times. Because of the complexity of the mechanical operation of many of these instruments and the intricacy of their works, it is often very difficult to be certain that the instrument is sterilized. This is especially true in many hospitals where the only technique for sterilization is auto-claving. To solve this problem, there have been developed disposable or single use versions of such repeating instruments. By making the instruments disposable, the re-sterilization problem is solved. Also, the instrument can be sterilized by various techniques; that is, cobalt irradiation, ethylene oxide, etc., under controlled conditions to insure that the instrument is sterile. However, by making the instrument disposable a number of other problems arise. First, it is desirable to make the disposable instrument out of inexpensive materials. Because of the complexity of the instrument and the mechanical movements required in these instruments, the requirements placed on these materials for certain uses is quite stringent. For example, the actuator or the driver which is going to repeatedly drive fasteners or set fasteners one after the other must be sufficiently strong and flexible to go through a sterilization procedure, be packaged, perhaps be stored for extended periods of time of 6 months, a year or more, remain sterile, and when put to use perform without even a minor flaw. Hence, to allow these disposable instruments to be made from some of the inexpensive plastic materials yet insure that a sterile, operable instrument is presented in the surgical theater, the packaging of the instrument is critical.

What I have discovered is a new and improved package for disposable instruments that have a repeating mode of operation. My new package allows the instrument to be stored and shipped while protecting all of its moving parts. My new package insures that the instrument when removed from the package is ready for use and will perform in the desire manner. My new package prevents dislodgment of the fasteners within the instrument and prevents dislodgment of the instrument within the package that might be harmful to the instrument and its function. The package is readily sterilizable and protects and maintains the instrument in a desired condition for extended periods of time.

SUMMARY OF THE PRESENT INVENTION

In accordance with the present invention, the new and improved package, for a sterile instrument having a repeating operation and utilizing a flexible driver, comprises an open, tray-like, semi-rigid, formed means for holding the instrument. A rigid means is mounted on the semi-rigid means for maintaining the instrument in a position where the driver is stored in an unstressed state to prevent the driver from taking an undesirable set over an extended period of time. An insert covers the open side of the semi-rigid formed means and provides ready access to the instrument. The instrument, semi-rigid formed means, rigid means and insert are surrounded by encasing means which maintain the instrument in a sterile environment. In preferred embodiments of the present invention, the rigid means is a metal means permanently mounted on the semi-rigid formed means. In certain embodiments of the present invention, flap means are connected to the semi-rigid formed means to at least partially cover the open side of the formed means to assist in maintaining the integrity of the package. In some embodiments of the present invention, the insert means comprises paper means disposed over the entire open side of the semi-rigid formed means and interlocking with the flap means. The paper means has a die cut portion which is torn upon opening the encasing means to provide access to the handling portion of the instrument. In certain preferred embodiments of the present invention, the encasing means with the semi-rigid formed means, rigid means, instrument, and insert therein are overwrapped in a tray for holding the encased instrument. The tray includes a lid member removably sealed around the periphery of the tray to maintain the encased instrument in a sterile environment. This overwrap allows a sterile package to be presented to a sterile environment and opened in such environment to present a sterile instrument.

BRIEF DESCRIPTION OF THE DRAWINGS

The invention will be more fully described in conjunction with the accompanying drawings wherein:

FIG. 1 is an exploded view in perspective of one embodiment of the new package of the present invention;

FIG. 2 is a plan view of the open front side of one portion of the package of the present invention;

FIG. 3 is a plan view of the opposite side of the portion of the package shown in FIG. 2;

FIG. 4 is a plan view of one type of insert that may be used in the package of the present invention;

FIG. 5 is a plan view of one type of instrument that may be packaged in the package of the present invention; and FIG. 6 is a side view of the instrument shown in Figure 5.

DETAILED DESCRIPTION OF THE DRAWINGS

Referring to FIG. 1 of the drawings, there is shown one embodiment of the package of the present invention. In this embodiment, an instrument 10 is held in a thermally formed polypropylene holding means 11. The holding means is a support tray with an open top. As more clearly shown in FIGS. 2 and 3, the tray has formed areas 12, 13, and 14 which frictionally engage portions of the instrument to hold the instrument in place in a desired position. The thermally formed means includes a flap means 15 connected along a portion of one edge of the tray and which folds over on top of the instrument and partially closes the open side of the tray. Cooperating with the thermally formed tray is a rigid means 16 which sits in the reverse hollow areas of areas 12 and 13 of the thermally formed tray and cooperates with those areas to hold the instrument in the desired position in the tray even while the tray is being sterilized, shipped, handled, etc. In this embodiment, the rigid means is a stainless steel member having a flat area 17 and two projecting legs 18 and 19 which are inserted in the reverse hollow areas in the thermally formed tray and it is the walls of these areas that contact the instrument. The thermally formed polypropylene tray sits in a formed foil tray 20. The formed foil tray is made of a two mil aluminum foil which is Mylar* reinforced and which has a vinyl heat seal coating on one surface that comprises the outer periphery of the tray. Positioned on top of the thermally formed tray 11 is a paper insert member 21. The insert member is more clearly shown in FIG. 4. This paper insert member serves primarily to provide for easy or ready access to the instrument as will be more fully described hereinafter. Also, if the instrument is using fasteners made from absorbable polymers that are hydrolyzable, it is important that the polymers be kept as dry as possible. This may be accomplished by placing a dessicant in the enviornment with the absorbable polymer fasteners and the paper insert may act as such a dessicant. The insert includes openings 22 superimposed over the openings in the flap 23 to provide for circulation of gases throughout the entire package during sterilization. The insert also includes two cut-out portions 24 and 25 which position the insert correctly with regard to the flap 15 and the thermally formed tray 11. The insert includes a die cut area 27 and a pair of tabs 26 and 28. The tabs are caught or inserted in the periphery of the outer wrapping so that when the outer wrapping is torn where indicated the tab 28 also tears and the paper insert is torn across the die cut area. A foil top member 30 made of material similar to the foil tray is positioned over the paper insert and is heat sealed to the periphery of the formed foil tray to totally encase the instrument, formed holding means, rigid holding means, and paper insert.

If the materials are such that it is desirable or necessary to sterilize the materials utilizing ethylene oxide, as is very often the case with certain absorbable polymers as well as certain materials used in making the package or the instrument, this may be accomplished at this point by leaving one end of the foil package open and sterilizing the package utilizing ethylene oxide as is well known in the art. The end of the package is left open because of the impermeability of the package and the requirement that the ethylene oxide circulate in and around the instrument, etc. Once the package has been sterilized with ethylene oxide, it is a simple matter to seal the open end to produce a packaged sterile instrument. The package is overwrapped in a second thermo formed outer tray 31 in which the encased instrument package is positioned. The shape of the depression 32 in the outer tray is such as to readily allow a hand to grasp the inner package. This outer tray also may be made from polypropylene or other suitable material. The lid 33 for the tray is made of Tyvek* fabric, fabric sold by DuPont and which is a polyolefin spunbonded material. The Tyvek lid is sealed to the outer periphery of the thermoplastic tray by a peelable seal which may be readily opened from one end 34. The entire package is sterilized again using ethylene oxide. As the Tyvek material is permeable to the ethylene oxide gas, there is no necessity to leave an open area for circulation and it is a simple matter to sterilize the final sealed package.

In use, the nurse simply opens the outer package thus presenting the sterile inner package which can be placed on an appropriate operating room table or cart and opened in a sterile environment within the operating room to produce a sterile instrument ready for use.

Thermally formed support trays are preferably made from polypropylene as polypropylene leaves no residual matter when sterilized utilizing ethylene oxide. The support tray holds a stainless steel means which keeps the instrument in a closed position when in the support tray. The tray prevents the steel means from scratching the instrument and it also keeps the steel means with the formed tray so that there are not a number of extra items in the operating room.

The top flap insures that the instrument is held in place during shipping and handling. The entire thermally formed tray prevents the crushing of the instrument and the package during sterilization. In the ethylene oxide sterilization, high vacuums are used and unless there is some stability to the package, it will collapse about the instrument during sterilization and be unsuitable. The thermo-formed tray and flap along with the paper insert prevent such a collapse.

In FIGS. 5 and 6 there is shown a repeating type instrument 40 used in surgical procedures. The specific instrument shown is used for ligating or occluding vessels and supplies a plurality of clips which may be closed about vessels by a repeating scissors type action. As shown in FIG. 5 the instrument includes a pair of handles 41 at one end and a set of jaws 42 at the opposite end. On actuating the handles; that is, on bringing the handles together, the jaws of the instrument are closed. A suitable repeating driver cooperates with the motion of opening and closing the handles to place clips 43 in the jaws; hence, in operation on closing the handles, a clip is closed by the jaws of the instrument and on releasing the handles the driver proceeds to place the next clip into the jaws of the instrument. Generally, the instruments are used deep within the surgical site and, hence, the jaws are very often curved or tilted so that they can be readily seen and the instrument itself does not obstruct the surgeon's view. This curve 44 is more clearly shown in FIG. 6. As can be appreciated, the driver must curve or bend when it places the clip in the jaws. Hence, if the instrument was packaged with the handles and the jaws open, the driver would be in its curved position. Because it is desirable to make these instruments disposable it is desirable that the parts be made of inexpensive materials. Generally, most plastic materials take a set if held in a position for any length of time and, hence, the driver would take the set of the curve of the jaws. This would mean that if the instrument were packaged in the open position, the driver would take this set in the jaws and the instrument would not be operable as that set would cause jamming of the driver. In accordance with the present invention, my package places the instrument in a specifically closed position so that the driver is moved backwards out of the jaws and is in a flat position, and does not take a permanent set. Also, it is not merely sufficient to close the instrument because at one point on that closing, the clips or fasteners are free or movable within the instrument. If the instrument is not held absolutely correctly in the specific closed position, the clips may fall out of the instrument or be dislodged from their track. My new package holds the instrument in the desired position and prevents dislodgment of the clip or other surgical devices to be placed by the instrument.

The instruments may be made from various materials such polyolefins, polystyrenes, or similar plastic materials or various metals or stiff paper materials or various combinations. The fasteners may be made of either metal such as stainless steel, tantalum, and the like or from various polymers of either the absorbable or nonabsorbable variety.

The parts of the package may be made from various thermally formable plastic materials as well as various films and papers, foils, and various combinations of the same depending on the portion of the package and the type of instrument to be packaged as well as the type of sterilization to be used. The selection of materials and combinations of materials as well as the method of sealing, etc. are well within the skill of one skilled in the art of packaging such sterilizable surgical products.

Having now described the present invention, it will be understood by those skilled in the art that variations and modifications of the specific embodiments described above may be employed without departing from the spirit and scope of the present invention as defined in the appended claims.

What is claimed is:

1. A package for a sterile instrument, said instrument having a repeating type operation utilizing a flexible driver, said package comprising;
    semi-rigid formed means for holding said instrument;
    rigid means mounted on said formed means for maintaining said instrument in a position wherein the driver is maintained in an unstressed state to prevent it from taking a permanent set;
    an insert covering one side of said semi-rigid formed means for providing ready access to said instrument; and
    encasing means for completely surrounding said instrument, semi-rigid formed means, rigid means, insert, and access means for maintaining said instrument sterile.

2. A package according to claim 1 wherein the semi-rigid formed means is an open, polypropylene tray.

3. A package according to claim 1 or 2 wherein the rigid means is a stainless steel member.

4. A package according to claim 1, 2, or 3 wherein the insert is a paper insert.

5. A package for a sterile instrument, said instrument having a repeating type operation wherein a flexible driver repeatedly feeds a plurality of fasteners moveable on a track in the instrument to the operating jaws of the instrument, said package including rigid means cooperating with said instrument to maintain said instrument in a precise position wherein the flexible driver is maintained in an unstressed state while the package, and the plurality of fasteners are held in a position in the track.

6. A package for a sterile instrument, said instrument having a repeating type operation utilizing a flexible driver, said package comprising;
    semi-rigid formed means having an open top for holding said instrument;
    rigid means mounted on said formed means for maintaining said instrument in a position wherein the driver is in an unstressed state to prevent it from taking a permanent set;
    flap means connected to one edge of said semi-rigid formed means to at least partially cover the instrument to assist in maintaining the integrity of the package during sterilziation;
    insert means disposed over the flap means and covering the open top of the semi-rigid formed means;
    said insert engaging said flap means to lock said insert in place and said insert having a die cut portion for providing ready access to the instrument;
    encasing means completely surrounding said semi-rigid formed means, flap means, and paper insert for maintaining said instrument in a sterile environment;
    said encasing means comprising two pieces of foil having a thermo-plastic coating thereon and being heat sealed together about their periphery;
    a thermoplastic formed tray for holding said foil encased instrument and;
    a lid member removably sealed about the periphery of said tray to maintain said foil encased instrument in a sterile condition.

7. A package according to claim 6 wherein the semi-rigid formed means is a polypropylene tray.

8. A package according to claim 6 or 7 wherein the rigid means is a stainless steel member.

9. A package according to claim 6 or 8 wherein the insert is a paper isert.

10. A package according to claim 9 wherein a portion of the paper insert is sealed in the periphery of the two pieces of foil whereby on tearing the foil the insert is torn to expose the instrument.

* * * * *